United States Patent [19]
Diesen et al.

[11] Patent Number: 5,488,020
[45] Date of Patent: Jan. 30, 1996

[54] COPPER-IMPREGNATED ZEOLITE COMPOSITION

[75] Inventors: Ronald W. Diesen; Kenneth A. Burdett; Ravi S. Dixit; Stanley S. T. King, all of Midland, Mich.

[73] Assignee: The Dow Chemical Company, Midland, Mich.

[21] Appl. No.: 200,258

[22] Filed: Feb. 23, 1994

Related U.S. Application Data

[60] Division of Ser. No. 954,710, Sep. 30, 1992, Pat. No. 5,329,057, which is a continuation-in-part of Ser. No. 688,808, Apr. 19, 1991, Pat. No. 5,196,621.

[51] Int. Cl.$^6$ .................................................. C07C 2/50
[52] U.S. Cl. ........................ 502/60; 502/79; 585/366; 585/510; 585/530; 585/533
[58] Field of Search ........................................ 502/60, 79

[56] References Cited

U.S. PATENT DOCUMENTS

| | | | |
|---|---|---|---|
| 3,013,982 | 12/1961 | Breck et al. | 252/455 |
| 3,013,982 | 12/1961 | Breck et al. | 252/455 |
| 3,013,985 | 12/1961 | Breck et al. | 502/79 |
| 3,013,985 | 12/1961 | Breck et al. | 252/455 |
| 3,013,985 | 12/1961 | Breck et al. | 252/455 |
| 3,181,231 | 5/1965 | Breck | 29/182.5 |
| 3,181,231 | 5/1965 | Breck | 29/182.5 |
| 3,200,082 | 8/1965 | Breck et al. | 252/455 |
| 3,200,082 | 8/1965 | Breck et al. | 252/455 |
| 3,236,761 | 2/1966 | Rabo et al. | 502/74 |
| 3,444,253 | 5/1969 | Reimlinger et al. | 260/666 |
| 3,444,253 | 5/1969 | Reimlinger et al. | 260/666 |
| 3,471,412 | 10/1969 | Miale et al. | 252/439 |
| 3,471,412 | 10/1969 | Miale et al. | 252/439 |
| 3,497,462 | 2/1970 | Kruerke | 252/454 |
| 3,497,462 | 2/1970 | Kruerke | 252/454 |
| 3,497,462 | 2/1970 | Kruerke | 502/79 |
| 3,547,831 | 12/1970 | Oleck et al. | 252/455 |
| 3,547,831 | 12/1970 | Oleck et al. | 252/455 |
| 3,755,540 | 8/1973 | Rosback | 423/328 |
| 3,755,540 | 8/1973 | Rosback | 423/328 |
| 3,756,964 | 9/1973 | Frazee et al. | 252/454 |
| 3,756,964 | 9/1973 | Frazee et al. | 252/454 |
| 3,835,068 | 9/1974 | West | 252/455 Z |
| 3,835,068 | 9/1974 | West | 252/455 Z |
| 3,929,621 | 12/1975 | Lussier et al. | 208/120 |
| 3,929,621 | 12/1975 | Lussier et al. | 208/120 |
| 4,019,880 | 4/1977 | Rabo et al. | 55/68 |
| 4,019,880 | 4/1977 | Rabo et al. | 55/68 |
| 4,034,065 | 7/1977 | Kasai et al. | 502/60 |
| 4,125,483 | 11/1978 | Downing et al. | 252/455 R |
| 4,125,483 | 11/1978 | Downing et al. | 252/455 R |
| 4,126,643 | 11/1978 | Paxson et al. | 260/673 |
| 4,126,643 | 11/1978 | Paxson et al. | 260/673 |
| 4,166,076 | 8/1979 | Roobeek et al. | 585/366 |
| 4,166,076 | 5/1979 | Rodbeek et al. | 585/366 |
| 4,226,812 | 10/1980 | Pieters et al. | 570/157 |
| 4,226,812 | 10/1980 | Pieters et al. | 570/157 |
| 4,278,650 | 7/1981 | Dorrance | 423/579 |
| 4,278,650 | 7/1981 | Dorrance | 423/579 |

(List continued on next page.)

FOREIGN PATENT DOCUMENTS

| | | |
|---|---|---|
| 0261730 | 3/1988 | European Pat. Off. . |
| 0393917 | 10/1990 | European Pat. Off. . |
| 1488521 | 10/1977 | United Kingdom . |
| 1554942 | 10/1979 | United Kingdom . |

OTHER PUBLICATIONS

Maxwell et al., "Copper–Exchanged Zeolite Catalysis for the Cyclodimerization of Butadiene," *Journal of Catalysis*, 61, 493–502 (1980).

Maxwell et al., "A Kinetic Study of the Reduction of Divalent Copper–Exchanged Faujasite with Butadiene and Ammonia," *Journal of Catalysis*, 41, 412–419 (1976).

CA 71889A/40 Moscow Lomonosov Univ (1975).

CA 58:10775 "Highly Active Catalysts" (1962).

CA 89:179172v (1978).

Renger et al., "The Cyclodimerization of Butadiene on Cu–SiO$_2$ Catalysts," *Z. Chem.*, 19(5), 194–195 (1979).

Maxwell et al., "Copper–Exchanged Zeolite Catalysts for the Cyclodimerization of Butadiene," *Journal of Catalysis*, 61, 485–492 (1980).

Reimlinger et al., "Notiz über die Synthese von 1–Vinyl–cyclohexen–(3) und Cyclohexadien–(1,4) durch zeolith katalysierte Diels Alder Reaktionen," *Chem. Ber.*, 103, 2317–2319 (1970).

Renger et al., "The Cyclodimerization of Butadiene on Cu–SiO$_2$ Catalysts," *Z. Chem.*, 19(5), 194–195 (1979). (Translation attached).

Maxwell et al., "Copper–Exchanged Zeolite Catalysts for the Cyclodimerization of Butadiene," *Journal of Catalysis*, 61, 485–492 (1980).

Maxwell et al., "Copper–Exchanged Zeolite Catalysis for the Cyclodimerization of Butadiene," *Journal of Catalysis*, 61, 493–502 (1980).

Maxwell et al., "A Kinetic Study of the Reduction of Divalent Copper–Exchanged Faujasite with Butadiene and Ammonia," *Journal of Catalysis*, 41, 412–419 (1976).

CA 71889A/40 Moscow Lomonosov Univ (1975).

CA 58:10775 "Highly Active Catalysts" (1962).

CA 89:17917v (1978).

I. E. Maxwell and E. Drent, Journal of Catalysis 41, 412–419 (1976), "A Kinetic Study of the Reduction of Divalent Copper–Exchanged Faujasite with Butadiene and Ammonia".

*Primary Examiner*—Asok Pal
*Attorney, Agent, or Firm*—John B. Treangen

[57] ABSTRACT

A composition comprising a copper(I) impregnated aluminosilicate zeolite wherein the zeolite is selected from faujasites, L and Ω, and wherein the zeolite has a silica to bulk alumina molar ratio between about 12 and about 50 and a silica to framework alumina molar ratio of at least about 15. The catalyst preparation involves in the following order: drying the selected zeolite, impregnating the dried zeolite with a copper(II) salt, calcining the copper(II)-impregnated zeolite, and reducing the copper(II) to copper(I). The composition is useful as a catalyst for the cyclodimerization of 1,3-butadiene to 4-vinylcyclohexene.

17 Claims, 3 Drawing Sheets

U.S. PATENT DOCUMENTS

| | | | |
|---|---|---|---|
| 4,347,164 | 8/1982 | Scherzer | 252/455 Z |
| 4,348,272 | 9/1982 | Tu | 208/111 |
| 4,348,272 | 9/1982 | Tu | 208/111 |
| 4,384,153 | 5/1983 | Dessan | 585/366 |
| 4,384,153 | 5/1983 | Dessan | 585/366 |
| 4,413,154 | 11/1983 | Dessau | 585/366 |
| 4,413,154 | 11/1983 | Dessau | 585/366 |
| 4,500,646 | 2/1985 | Denise et al. | 502/78 |
| 4,500,646 | 2/1985 | Denise et al. | 502/78 |
| 4,513,092 | 4/1985 | Chu et al. | 502/71 |
| 4,513,092 | 4/1985 | Chu et al. | 502/71 |
| 4,552,855 | 11/1985 | Ozin et al. | 502/74 |
| 4,552,855 | 11/1985 | Ozin et al. | 502/74 |
| 4,665,247 | 5/1987 | Dessau | 585/361 |
| 4,665,247 | 5/1987 | Dessau | 585/361 |
| 4,783,433 | 11/1988 | Tajima et al. | 502/74 |
| 4,783,433 | 11/1988 | Tajima et al. | 502/74 |
| 4,783,433 | 11/1988 | Tajima et al. | 502/60 |
| 4,814,527 | 3/1989 | Diesen | 570/243 |
| 4,814,527 | 3/1989 | Diesen | 570/243 |
| 4,910,176 | 3/1990 | Diesen | 502/64 |
| 4,917,711 | 4/1990 | Xie et al. | 502/60 |
| 4,917,711 | 4/1990 | Xie et al. | 55/68 |
| 4,917,711 | 4/1990 | Xie et al. | 55/68 |
| 5,095,082 | 3/1992 | Kelsey | 585/361 |
| 5,095,082 | 3/1992 | Kelsey | 585/361 |
| 5,196,621 | 3/1993 | Diesen et al. | 585/361 |
| 5,196,621 | 3/1993 | Diesen et al. | 585/361 |
| 5,200,376 | 4/1993 | Saint Just et al. | 502/60 |

"k vs Wt % Water"

COPPER-IMPREGNATED ZEOLITE COMPOSITION

This application is a divisional of application Ser. No. 07/954,710, filed Sep. 30, 1992, now U.S. Pat. No. 5,329,057, which is a continuation-in-part of application Ser. No. 07/688,808, filed Apr. 19, 1991, now U.S. Pat. No. 5,196,621.

BACKGROUND OF THE INVENTION

This invention pertains to a process for the cyclodimerization of 1,3-butadiene or substituted 1,3-butadienes to 4-vinylcyclohexene or a substituted derivative thereof.

4-Vinylcyclohexene (hereinafter referred to as vinylcyclohexene) and substituted vinylcyclohexenes are useful starting materials for the synthesis of styrene and substituted styrenes. Styrene is a well-known monomer for polystyrene plastics and composites.

Catalyzed processes are known for the dimerization of butadiene. For example, British Patent 1,554,942 and U.S. Pat. No. 4,125,483 disclose a process for the catalytic dimerization of butadiene to vinylcyclohexene in the presence of a cation-exchangeable aluminosilicate into which copper(I) ions and ions of an alkali metal having an atomic number of at least 19, preferably, cesium, have been introduced. The aluminosilicate includes natural and synthetic zeolites, such as faujasite, as well as clay minerals, such as montmorillonite, and other synthetic silica aluminas. It is taught that copper is introduced into the aluminosilicate via ion-exchange with a copper(I) or copper(II) salt.

U.S. Pat. No. 3,444,253 also discloses the dimerization of butadiene to vinylcyclohexene in the presence of copper(I) zeolites X or Y. The catalyst is taught to be prepared by ion-exchange of sodium zeolite X or Y with cuprous iodide in liquid ammonia or by the reduction of copper(II) zeolite X or Y with carbon monoxides ammonia, acetylenic hydrocarbon or an olefinic hydrocarbon.

U.S. Pat. No. 4,664,247 relates to a process for the cyclodimerization of butadiene to vinylcyclohexene under Diels-Alder conditions in the presence of a copper-containing ZSM-12 zeolite catalyst. It is taught that the ZMS-12 zeolite is ion-exchanged or impregnated with copper(II) cation.

P. Renger, R. Janowski, F. Wolf and E. Jahn report in Z. Chem., 19 (1979), 194–195, that butadiene is cyclodimerized to vinylcyclohexene in the presence of silica gel impregnated with copper(II) cations.

All of these processes suffer from the same manifold disadvantages. First, and most importantly, the lifetime of these catalysts is short, and the catalyst easily deactivates from coking and fouling. Second, the preparations of the catalysts are difficult and expensive. For examples the catalysts prepared by ion-exchange with copper(II) salts must be reduced to the copper(I) oxidation state, which is the active form of the catalyst. Disadvantageously, the reduction process in the ion-exchanged material is inefficient. Alternatively, the catalysts may be prepared without reductants by ion-exchange with copper(I) salts; however, this route is disadvantageous because copper(I) salts oxidize easily and are not readily solubilized without expensive solubilizing ligands. Third, regeneration of these catalysts typically requires burning off the coked material at high temperatures, usually at least about 400° C. Such a procedure oxidizes copper(I) to copper(II), and therefore a reduction procedure is again necessitated to bring the catalyst back into the active cuprous form. Finally, in certain instances the catalysts may possess low activity and even low selectivity.

SUMMARY OF THE INVENTION

In a first aspect this invention is a process for the cyclodimerization of 1,3-butadiene or substituted 1,3-butadiene to 4-vinylcyclohexene or a substituted derivative thereof. The process comprises contacting 1,3-butadiene or a substituted 1,3-butadiene with a catalytic amount of a copper(I)-aluminosilicate zeolite prepared as described hereinbelow. The zeolite is selected from the group consisting of faujasites, mordenite, zeolite L, zeolite $\Omega$, and zeolite beta. The contacting of the butadiene and the copper(I)-zeolite occurs under reaction conditions such that 4-vinylcyclohexene or a substituted derivative thereof is formed.

The copper(I)-aluminosilicate zeolite employed in the first aspect of this invention can be prepared by one of three general methods. In the first method, a dried aluminosilicate zeolite selected from the group consisting of faujasites, mordenite, zeolite L, zeolite $\Omega$, and zeolite beta and having a framework silica to alumina molar ratio of at least about 15 is impregnated with a solution of a copper(II) salt. Thereafter, the copper(II)-impregnated zeolite is calcined under reaction conditions sufficient to remove the anion of the copper salt. After calcination the copper(II)-impregnated zeolite is reduced under reaction conditions such that a portion of the copper(II) ions are converted to copper(I). As a second method, the catalyst can be prepared by heating a solid mixture containing a copper salt and the above-identified aluminosilicate zeolite in the absence of liquid solvent. As a third method, the catalyst can be prepared by contacting vapors of a copper salt with the above-mentioned aluminosilicate zeolite.

In a second aspect this invention is a process for the cyclodimerization of butadiene or substituted 1,3-butadiene to 4-vinylcyclohexene or a substituted derivative thereof. The process comprises contacting 1,3-butadiene or a substituted 1,3-butadiene with a catalytic amount of copper(I) ions supported on a carrier. The contacting also occurs in the presence of a promoting amount of a hydroxylic solvent and under reaction conditions such that the activity of the catalyst, as measured by the rate constant for the formation of vinylcyclohexene, is increased when compared to a control process conducted with a minimum level of hydroxylic solvent. The control process and minimum hydroxylic solvent level are described in detail hereinafter.

The processes of this invention produce vinylcyclohexenes in a steady high rate of formation, heretofore not possible with the catalysts of the prior art. Vinylcyclohexenes are valuable as precursors to styrenes. In addition, the preferred catalysts in the process of this invention possess many advantageous features, described hereinbelow.

In a third aspect, this invention is a catalyst composition comprising copper(I) ions impregnated onto an aluminosilicate zeolite. The zeolite is selected from the group consisting of faujasites, mordenite, zeolite L, zeolite omega ($\Omega$), and zeolite beta ($\beta$). The zeolite is characterized by a silica to bulk alumina molar ratio in the range from about 5 to about 50, and a silica to tetrahedral framework alumina molar ratio of at least about 15. The "bulk" ratio includes alumina from both tetrahedral framework sites as well as excess or non-framework alumina located in the pores. Optionally, the catalyst composition contains a binder.

In a fourth aspect, this invention is a method of preparing the above-identified catalyst comprising (a) drying an aluminosilicate zeolite to remove water, the zeolite being selected from the group consisting of faujasites, mordenite, zeolite L, zeolite Ω and zeolite β and being characterized by a silica to bulk alumina molar ratio in the range from about 5 to about 50 and a silica to framework alumina molar ratio of at least about 15, (b) impregnating the dried zeolite with a solution containing a copper(II) salt, (c) calcining the copper(II)-impregnated zeolite under conditions such that the anion of the soluble salt is removed, and (d) reducing the calcined copper(II)-impregnated zeolite under conditions such that a portion of the copper(II) ions are converted to copper(I). Optionally, a promoting amount of hydroxylic solvent may be added after calcination and prior to reduction.

The catalyst of this invention is useful in the aforementioned cyclodimerization of butadiene and substituted butadienes, and surprisingly maintains a long lifetime in that process before deactivating. A catalyst half-life on the order of at least about 200 hours is readily achieved. In addition, the above-identified catalyst is advantageously prepared without expensive solubilizing ligands. More advantageously, the reduction of the copper(II)-zeolite catalyst precursor prepared by this invention is efficient. In some preparative embodiments, a separate reduction step is not required or the reduction is conducted in situ in the aforementioned cyclodimerization process. Most advantageously, the catalyst of this invention is easily regenerated. All that is required is an oxygen burn-off at low temperatures, typically less than about 350° C., followed by reduction, and the activity of the catalyst is restored essentially to its original level. Consequently, the combined beneficial properties of the catalyst of this invention make it desirable for commercial applications.

Figure 1:
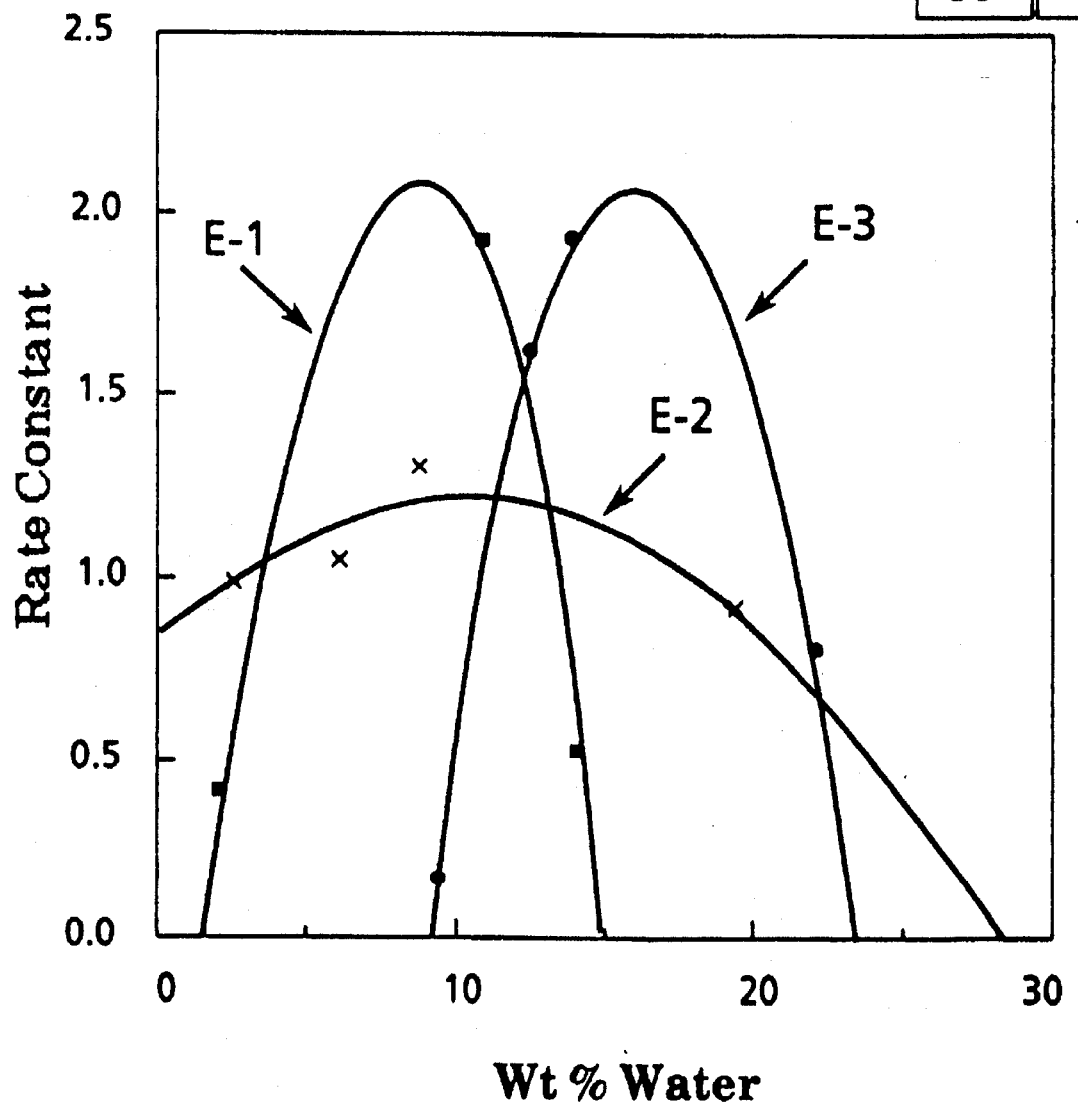
FIGS. 1, 2 and 3 depict graphs of the rate constant for the formation of vinylcyclohexene plotted versus the concentration of water in the catalyst, as described in detail in Examples E-1(a–b), E-2(a–d), E-3(a–f), E-4(a–i), and E-9(a–f).

DETAILED DESCRIPTION OF THE INVENTION 1,3-Butadiene or a substituted 1,3-butadiene is required for the cyclodimerization processes of this invention. 1,3-Butadiene may be obtained from any hydrocarbon source. Crude C4 hydrocarbon feedstreams obtained from petroleum crackers are suitable. Preferably, the crude C4 hydrocarbon stream contains from about, 10 volume percent to about 80 volume percent 1,3-butadiene. The balance of such streams comprises predominantly butane with lesser amounts of butenes, methylallene, methylacetylene, and other C4 compounds. More preferably, the concentration of butadiene in the feedstream ranges from about 30 volume percent to about 50 volume percent. Optionally, it may be desirable to purify the crude C4 hydrocarbon stream over a copper hydrogenation catalyst, such as a KLP-type catalyst, to remove acetylenic components which may cause a problem in the cyclodimerization process.

Substituted 1,3-butadienes are also suitable for the cyclodimerization processes of this invention. The substituent may be situated at any carbon along the butadiene chain, but preferably is substituted at the 2-carbon. The substituent is required to be inert, meaning that it does not inhibit the cyclodimerization process of this invention. Suitable substituents include a alkyl moieties, preferably containing from 1 to about 10 carbon atoms, as well as halo moieties, such as chloro and bromo, and amino, nitro, and hydroxyl moieties. Non-limiting examples of substituted 1,3-butadienes include isoprene and chloroprene. Preferably, the substituted 1,3-butadiene is isoprene.

Optionally, a liquid diluent can be employed with the above-identified butadiene feedstream. The primary function of the diluent is to reduce the concentration of vinylcyclohexene in the product stream, because at high concentrations vinylcyclohexene can reduce catalytic activity. Such liquid diluents should be stable and inert with respect to the cyclodimerization processes of this invention. Suitable diluents include aromatic hydrocarbons, preferably, those having one aromatic ring and up to about 15 carbon atoms. Nonlimiting examples include benzene, toluene, xylene, ethylbenzene, and propylbenzene; however, other solvents such as naphthalene, nitrobenzene, ethylene dichloride, n-butane and butenes are also suitable. Preferably, the diluent is ethylbenzene or propylbenzene. More preferably, the diluent is ethylbenzene. If a diluent is used, then the concentration of butadiene in the feedstream containing the diluent ranges, preferably, from about 10 volume percent to about 80 volume percent, as noted hereinbefore. Below about 10 volume percent, the conversion of butadiene may be too low and the process may be economically unfeasible. Above about 80 volume percent, the process may be difficult to control and the high concentration of vinylcyclohexene product may reduce catalytic activity.

A hydroxylic solvent is required for the second cyclodimerization process of this invention. The hydroxylic solvent is any liquid containing hydroxyl moieties, such as water and alcohols. Preferred alcohols are lower molecular weight mono-alcohols containing up to about five carbon atoms, such as methanol, ethanol, n-propanol, i-propanol, t-butanol, n-pentanol, and the like. More preferably, the hydroxylic solvent is water or an alcohol containing up to about three carbon atoms. Most preferably, the hydroxylic solvent is water or methanol.

The hydroxylic solvent may be added either to the feedstream or to the catalyst. Preferably, however, the hydroxylic solvent is initially added to the catalyst, and the feedstream is kept just hydroxylated enough to maintain the desired hydroxyl level on the catalyst under the operating conditions of the process. Preferably, the concentration of the hydroxylic solvent in the feedstream is less than about 250 ppm, more preferably, less than about 100 ppm, most preferably less than about 50 ppm. A detailed description of how hydroxylic solvent is introduced into the catalyst is given hereinafter.

The catalyst employed in the process of this invention comprises copper(I) ions supported on a carrier. The carrier may be a crystalline aluminosilicate zeolite, a non-zeolitic amorphous aluminasilica mixture, silica, silica gel, alumina, or a clay mineral, such as montmorillonite. Preferably, the carrier is a crystalline aluminosilicate zeolite, any of the natural or synthetic varieties of which is suitable. Preferably, the carrier is selected from the group consisting of faujasite zeolites, mordenite, zeolite omega (Ω), zeolite L and zeolite beta (β). Even more preferably, the zeolite is selected from the group consisting of faujasite zeolites and zeolite L, and most preferably, faujasite zeolites X and Y. Copper ions may be introduced onto the support by techniques known to those skilled in the art, for example, ion-exchange, impregnation, and vapor-solid or liquid-solid reaction. These techniques are illustrated in detail hereinafter for the preferred case of a zeolite carrier.

The starting zeolite may be selected in an acid form or in a salt form, wherein the cation is typically an ion from the Group IA or IIA metals, such as sodium or magnesium ions. While any silica to bulk alumina molar ratio ($SiO_2/Al_2O_3$) is acceptable, the preferred starting zeolite has a bulk $SiO_2/Al_2O_3$ molar ratio ranging from about 5 to about 50. The aforementioned "bulk" ratio includes alumina from both tetrahedral framework sites as well as excess or non-framework alumina located in the pores. More preferably, the bulk $SiO_2/Al_2O_3$ molar ratio ranges from about 10 to about 45, most preferably, from about 12 to about 30. Below the preferred bulk $SiO_2/Al_2O_3$ molar ratio of about 5 the catalyst may have acceptable activity, but may exhibit a reduced lifetime. Above the preferred bulk $SiO_2/Al_2O_3$ molar ratio of about 50 the catalyst may have an acceptable lifetime, but may exhibit reduced activity. If only tetrahedral framework alumina is considered, the preferred framework $SiO_2/Al_2O_3$ molar ratio is at least about 15, more preferably, at least about 22.

The starting zeolite carriers of this invention are available commercially or can be synthesized according to procedures well documented in the art. See, for example, *Zeolite Molecular Sieves* by Donald W. Breck, john Wiley & Sons, 1974, and references therein. Zeolite carriers, such as the faujasites, mordenite, zeolite L and zeolite Ω, normally contain a significant quantity of water. For example, the faujasites taken as the sodium salt, typically can be represented by an oxide formula $Na_2O.Al_2O_3.4.5SiO_2.7H_2O$ which corresponds to a saturation water content of about 23 weight percent. Mordenite, taken as the sodium salty typically can be represented by an oxide formula $Na_2O.Al_2O_3.10SiO_2.6H_2O$ corresponding to a saturation water content of 12 weight percent. Zeolite L, taken as the sodium salt, can be represented by an oxide formula $Na_2O.Al_2O_3.6SiO_2.5H_2O$ which corresponds to a saturation water content of about 15 weight percent. Zeolite Ω, also taken as the sodium salty can be represented by an oxide formula $Na_2O.Al_2O_3.7SiO_2.5H_2O$, which corresponds to a saturation water content of about 13 weight percent. Unexpectedly, it has now been discovered that the concentration of water affects the activity of the catalysts in the processes of this invention, and that the aforementioned saturation level of water normally found in zeolites is detrimental to the activity of the catalyst.

Generally, therefore, the starting zeolite is dried prior to preparing the catalyst composition. This drying procedure is optional, but functions to remove most of the water from the zeolite. Drying is usually effected at a temperature in the range from about 50° C. to about 450° C., and preferably in a range from about 100° C. to about 300° C., for a time ranging from about 1 hr to about 24 hr. Usually, drying under these conditions reduces the water content of the zeolite to less than 2 weight percent.

The carrier may be used as is or may be composited with a binder into extrudate or pellets for added strength and durability. Binders such as silica, and alumina are suitable. Preferably, the binder is alumina. The size of the extrudate or pellets suitably ranges from about 1/32 inch to about 1/2 inch at largest dimension.

As noted hereinbefore, copper(I) ions are an essential component of the catalyst. Ion-exchange, impregnation, vapor-solid and liquid-solid reactions, described hereinafter, may be employed to introduce copper into the zeolite. In the case of ion-exchange and impregnation, typically, a water-soluble copper(II) salt is employed because copper(I) salts are not sufficiently soluble or stable, especially in water. It will be immediately obvious that if a copper(II) salt is ion-exchanged or impregnated into the zeolite, then a reduction step is required to obtain copper(I), the more active form of copper.

The concentration of copper(II) ions introduced into the carrier may be any concentration which yields a catalyst of high activity in the process of this invention, as defined hereinafter. Generally, the concentration ranges from about 0.1 to about 15 weight percent, preferably, from about 2 to about 9 percent, more preferably, from about 3 to about 8 percent.

In preferred embodiments, it is desirable for the copper(I)-catalyst to be essentially free of certain metals or metal ions, specifically, zinc, nickel, cesium and chromium. Even more preferably, it is desirable for the impregnated catalyst to be essentially free of chloride. By "essentially free" is meant that the concentration of these components in the catalyst is less than about 1 weight percent, more preferably, less than about 0.5 weight percent, most preferably, less than about 0.1 weight percent.

Ion-Exchange Method of Preparing Catalyst

The term "ion-exchange" is taken to mean a technique whereby metal ions, specifically copper ions in this case, actually replace a portion or essentially all of the hydrogen ions or cations of the zeolite. Ion-exchange is easily effected by stirring or slurrying the zeolite with an excess of a solution containing a soluble copper(II) salt. Non-limiting examples of suitable solutions include aqueous solutions of cupric nitrate, sulfate or acetate. The concentration of such solutions will vary depending upon the desired degree of ion-exchange, but typically range from about 0.01M to about 10M. Heat may be applied to enhance the replacement reaction. Typical temperatures range from about ambient to the boiling point of the solvent, preferably from about 50° C. to about 100° C. The slurrying time will depend upon the size of the batch, and therefore can vary widely. Generally, at least about 2 hours is required. Ion-exchange techniques are described by D. W. Breck in Zeolite Molecular Sieves: Structure, Chemistry and Use, Wiley-Interscience, 1974, Chapter 7, which is incorporated herein by reference. Alternatively, the catalyst may be prepared by direct ion-exchange with a copper(I) salt dissolved in liquid ammonia.

Optionally, when the catalyst is prepared by ion-exchange the zeolite may be ion-exchanged first with a Group IIA alkaline earth metal ion and thereafter ion-exchanged with a copper(II) salt. It is believed that the alkaline earth ions prohibit copper ions from migrating into deep, inaccessible sites in the zeolite where they may be less catalytically active. Such a theory, however, should not be binding. The preferred alkaline earth ions include magnesium, calcium, strontium, and barium ions, more preferably, calcium ions. The ion-exchange procedure is carried out with a soluble salt of the alkaline earth metal, for example, the nitrate, sulfate or acetate, in accordance with the exchange procedure described hereinbefore. The concentration of calcium ions in the zeolite ranges from about 0.05 to about 10 weight percent.

After the starting zeolite is ion-exchanged with copper(II) ions, the zeolite is usually dried at a temperature in the range from about 50° C. to about 120° C. to remove excess and adsorbed solvent. Thereafter, the ion-exchanged zeolite is reduced to convert a portion of the copper(II) ions to copper(I) ions. The reduction may be carried out with any reducing agent that is capable of this conversion. Non-limiting examples of reducing agents include hydrogen, carbon monoxide, ammonia, hydrazine, and ascorbic acid. Preferably, the reducing agent is gaseous ammonia or hydrazine in combination with a base, such as sodium hydroxide.

More preferably, the reducing agent is ammonia. The reduction is conducted at a temperature in the range from about 200° C. to about 400° C. and a pressure from about atmospheric to about 5 psig. Typically, at least about 10 percent of the copper(II) ions available to the reductant are converted to copper(I), preferably, at least about 50 percent of the copper(II) ions available to the reductant are converted to copper(I). The copper(I) ion-exchanged zeolite is thereafter treated with a promoting amount of hydroxylating solvent, as described hereinbelow.

Vapor-Solid and Liquid-Solid Reaction Method of Preparing Catalyst

As a second method of preparing the catalyst of this invention, a vapor-solid or liquid-solid reaction may be employed. In the vapor-solid reaction, a copper salt is heated to a temperature sufficient to generate a measurable vapor pressure of the salt, and the vapors are then contacted with the zeolite. Suitable copper salts include any which generate a measurable vapor pressure at a temperature below the decomposition temperature of the salt. Copper(I) and copper(II) salts are both acceptable. Non-limiting examples of suitable salts include cuprous halides, such as cuprous fluoride, cuprous chloride, cuprous bromide, and cuprous iodide; cuprous oxide; cuprous carboxylates, such as cuprous carbonate and cuprous acetate; cupric halides, such as cupric fluoride, cupric chloride, cupric bromide, and cupric iodide, cupric oxide; cupric carboxylates, such as cupric acetate and cupric formate; as well as cupric sulfate, cupric nitrate, and the like. A mixture of such salts is also acceptable. Preferably, the copper salt is a cuprous or cupric halide or oxide. More preferably, the copper salt is cuprous chloride or cupric chloride. The temperature of heating is generally greater than 200° C., but lower than the decomposition temperature of the salt. Preferably, the temperature is in the range from about 250° C. to about 800° C., more preferably, in the range from about 350° C. to about 700° C. The heating is continued for a time sufficient to yield a copper concentration ranging from about 0.1 to about 15 weight percent, preferably from about 2 to about 9 weight percent. Preferably, the time ranges from about 15 minutes to about 5 hours.

Alternatively, one of the aforementioned copper salts may be mixed with the zeolite to form a solid mixture, which is then heated in the absence of liquid solvent to form in situ a neat melt or vapors of the salt. The mixture typically ranges from about 0.5 to about 50 weight percent copper salt, preferably, from about 5 to about 20 weight percent copper salt. The temperature and time of heating are noted hereinabove. In a more preferred embodiment, the solid mixture is heated at a temperature ranging from about 500° C. to about 700° C. for a time ranging from about 15 minutes to about 4 hours, and thereafter cooled to a temperature in the range from about 100° C. to about 150° C. The heating is conducted in the presence of an inert atmosphere, such as helium, nitrogen, or carbon dioxide. A reducing atmosphere, preferably ammonia, may be employed when the copper salt is a copper oxide. In these cases, ammonia has been found to reduce the temperature and time required for the reduction. Following reduction with ammonia, however, the catalyst should be heated under a flow of inert gas, such as nitrogen, at a temperature of at least about 250° C. to strip off excess ammonia. It is advisable to avoid any contact of these catalysts with moisture.

Catalysts prepared by the vapor-solid and liquid-solid reaction methods require no further treatment. Reduction of copper(II) to copper(I) is not necessary, because surprisingly the methods produce a copper(I)-zeolite regardless of the initial oxidation state of the copper salt. Moreover, in contrast to catalysts prepared by ion-exchange, it has now been found that water is not a particularly beneficial component of the catalysts prepared by the vapor-solid and liquid-solid reaction methods. Preferably, these catalysts contain no greater than about 3 weight percent water.

Impregnation Method of Preparing the Catalyst

In yet another preparative method, copper may be introduced into the zeolite via impregnation. Those skilled in the art will know that "impregnation" refers to a technique whereby a metal salt, in this instance a soluble copper(II) salt, is deposited on the surface and throughout the pore structure of the zeolite, but predominantly on the surface. Hence, after impregnation the zeolite contains the anion of the salt in addition to copper(II) cations. Impregnation can be effected by dipping the zeolite into an excess of a solution of a copper salt, such as the nitrate, acetate or sulfate. Preferably, more precise control is achieved by a technique called "dry impregnation" or "impregnation to incipient wetness." In this method the zeolite is sprayed with a quantity of the copper(II) solution corresponding to the total known pore volume, or slightly less. The dry impregnation technique is described by Charles N. Satterfield in *Heterogeneous Catalysis in Practice*, McGraw-Hill Book Company, 1980, p. 82–83, and is incorporated herein by reference. Alternatively, it is possible to impregnate the support with a copper(I) salt; however, this method of catalyst preparation is not preferred because, as noted hereinbefore, copper(I) salts are not readily solubilized.

After the starting zeolite is impregnated with a copper(II) salt, the zeolite is usually dried at a temperature in the range from about 50° C. to about 120° C. to remove excess and adsorbed solvent. At this stage the copper(II)-impregnated zeolite essentially comprises a solid mixture containing a copper(II) salt and a zeolite. Thereafter, the dried, impregnated zeolite is calcined under air to destroy or oxidize the anion of the copper salt. The calcination is conducted at a temperature in the range from about 200° C. to about 325° C., preferably from about 250° C. to about 300° C., for a time ranging from about 1 to about 24 hours.

After calcination, the impregnated copper(II) ions are reduced to copper(I). Any reducing agent which can accomplish the reduction efficiently is acceptable, including olefinic hydrocarbons, such as butene, propylene, and butadiene, alcohols, such as propanol, and aldehydes. Preferably, the reducing agent is an olefinic hydrocarbon, more preferably, butadiene, propylene or 1-butene, and most preferably, propylene or 1-butene. The reducing conditions are found to be specific to the reducing agent. For example, when butadiene is employed as both reducing agent and substituent to be cyclodimerized, the copper(II)-impregnated zeolite may be treated first with a promoting amount of hydroxylating solvent and thereafter reduced in situ under liquid phase conditions in the butadiene cyclodimerization reaction. When propylene or 1-butene is employed as reducing agent, the copper(II) impregnated zeolite can be reduced in a nitrogen stream containing 20 volume percent of the olefin at a temperature ranging from about 100° C. to about 140° C. No water beyond the low levels already present (less than 2 wt percent) is required when the reductant is propylene or 1-butene. After reduction the Cu(I)-zeolite is usually stripped under nitrogen gas at a temperature from about 100° C. to about 250° C. for a time ranging from about 30 minutes to about 12 hours.

Catalysts prepared by vapor-solid, liquid-solid and impregnation techniques have greatly improved properties and, therefore, are preferred over catalysts prepared by ion-exchange. Specifically, these improved catalysts are easily prepared without the use of expensive ligands. In addition, the impregnated catalysts can be efficiently reduced with olefinic hydrocarbons at low temperatures even reduced in situ in the dimerization process, thereby eliminating a separate or inefficient reduction step. Advantageously, catalysts prepared by vapor-solid and liquid-solid reaction do not need reduction. More advantageously, the improved catalysts are easily regenerated by a simple burn-off at temperatures less than about 325° C., followed by re-reduction of copper(II) to copper(I). If rehydroxylation is desired, as in certain impregnated species, the hydroxylating solvent may be added after the burn-off step. Most advantageously, the catalysts possess a long lifetime.

A promoting amount of hydroxylic solvent, such as water, is required for the second dimerization process of this invention. The hydroxylic solvent functions to increase the activity of the catalyst, as measured by an increase in the rate of formation of vinylcyclohexene. The hydroxylic solvent may be added in the liquid or vapor phase to the "dried" form of the ion-exchanged or impregnated carriers. "Dried" forms of the carriers are easily obtained. Specifically, during the aforementioned calcination of the copper(II)-impregnated zeolite to remove the anion of the copper salt, water is also removed yielding an essentially dry zeolite containing no greater than about 2 weight percent water. Likewise, during the aforementioned reduction of the Cu(II)-exchanged zeolite, water is removed yielding a zeolite containing similarly low levels of water. Some carriers in the "dried" form may contain essentially no water, and zeolites if handled with special precaution can be dried to water levels lower than 2 weight percent. To hydroxylate the impregnated or ion-exchanged carrier, the dried material is exposed to a humidified vapor, such as ambient air or a moist stream of nitrogen, for a time sufficient to adsorb the desired concentration of water. Alternatively, a predetermined amount of alcohol may be added to the dried, impregnated or ion-exchanged carrier.

The concentration of hydroxylic solvent introduced into the copper(II)-treated carrier may be any concentration which achieves an increase in the rate of formation of vinylcyclohexene, as compared with a control process described hereinafter. The concentrations which achieve this effect vary depending upon the type of carrier, the copper loading, the manner in which copper ions are introduced into the carrier, its $SiO_2/Al_2O_3$ molar ratio (where applicable), and whether alkaline earth cations are present. Roughly, the promoting hydroxyl concentration is in the range from about one-seventh to about one-half of the saturation water concentration of the specific zeolite employed, as determined by thermal gravimetric analysis (TGA). In the case of a copper-exchanged faujasite zeolite the promoting amount of water varies from about 2.5 to about 22 weight percent of the catalyst composition depending upon the method of copper introduction and reduction. For example, the more preferred water concentration for a copper(II)-exchanged zeolite reduced with liquid ammonia ranges from 4 to 14 weight percent, whereas, the more preferred concentration for a copper(II)-exchanged zeolite reduced with hydrazine ranges from 10 to 21 weight percent. For an impregnated faujasite the water concentration will typically range from 0.5 to about 16 weight percent depending upon the reductant employed to reduce copper(II) to (I). Preferably, when the Cu(II)-impregnated catalyst precursor is reduced with butadiene in situ, the water concentration ranges from 3 to about 14 weight percent, more preferably, about 4 to about 12 weight percent, and most preferably, from about 7 to about 9 weight percent. Preferably, when the Cu(II)-impregnated catalyst precursor is pre-reduced with 1-butene or propylene, the water concentration ranges from essentially 0 to no greater than about 6 weight percent. Below the lower preferred concentration and above the upper preferred concentration, the activity of these catalysts, as measured by the rate of formation of vinylcyclohexene, may decrease significantly. Variations in the optimum range of water concentration are within the scope of this invention and may have to be determined by one skilled in the art.

Advantageously, the copper(I)-zeolite catalysts prepared by the vapor-solid, liquid-solid and impregnation methods described hereinbefore exhibit a long lifetime before loss of activity. Typically, the catalyst half-life ($\tau\frac{1}{2}$) in the cyclodimerization process conducted in liquid phase at 100° C. is at least about 200 hours. For the purposes of this invention, the half-life is defined as the time it takes for the rate constant for the formation of vinylcyclohexene to be reduced by one-half. Preferably, the catalyst half-life is at least about 500 hours, more preferably, at least about 800 hours, even more preferably, at least about 1000 hr, and most preferably, at least about 1500 hours.

When any catalyst of this invention has lost sufficient activity so as to render it uneconomical, the deactivated catalyst is easily regenerated by calcination in the presence of air at a temperature in the range from about 200° C. to about 500° C. for a time sufficient to render the catalyst active again, usually overnight. Preferably, the calcination temperature ranges from about 250° C. to about 450° C., more preferably from about 250° C. to about 350° C. for an impregnated catalyst. The heating functions to burn off polymeric butadienes and coke, but also oxidizes copper(I) at least in part to copper(II). The oxidized composition must therefore be reduced to the catalytically active copper(I) form. In addition, the oxidized composition may have to be rehydroxylated to readjust the water concentration to within the desired range. In the case of the ion-exchanged catalyst, the reduction is carried out as described hereinbefore, for example, with ammonia or hydrazine, and then rehydroxylation is effected. In the case of the impregnated catalyst, the reduction is simply carried out with propylene or butene, and rehydroxylation is not necessary. Catalysts prepared by vapor-solid and liquid-solid reaction are given a burn-off followed by reduction, preferably, with ammonia. No hydroxylating agent is added in the latter case, but the catalyst is stripped at about 250° C. after reduction to remove excess ammonia.

Butadiene or substituted butadienes can be contacted with the catalyst of this invention in a reactor of any configuration, including batch-type reactors and continuous flow reactors, such as continuous plugged flow reactors, continuous stirred tank reactors (CSTR), fluidized bed reactors, riser reactors, and the like. Preferably, the reactor is a continuous plugged flow reactor. The feedstream containing the butadiene may be maintained in the gaseous or liquid states, preferably, the liquid state.

Any operable temperature is suitable for the dimerization processes of this invention provided that the process yields a vinylcyclohexene product in high selectivity. Typically, the process temperature ranges from about 70° C. to about 190° C. Preferably, the temperature ranges from about 80° C. to about 150° C., more preferably, from about 100° C. to about 130° C. Below the preferred lower temperature, the conversion may be too low, and the process may become uneconomical. Above the preferred upper temperature the rate of reaction may be too high and the reaction may be difficult to control. Such high temperatures may also lead to hot spots, coking on the catalyst, and formation of polymeric by-products.

Likewise, any operable pressure is suitable for the dimerization processes of this invention provided that the process yields a vinylcyclohexene product in high selectivity. When the process is conducted in the liquid phase, the pressure must be high enough to maintain the butadiene feedstream in the liquid phase at the operating temperature. Suitable pressures are those greater than about 100 psig. Preferably, the pressure ranges from a,out 100 psig to about 1000 psig, more preferably, from about 200 psig to about 600 psig, most preferably, from about 300 psig to about 500 psig. Below the lower preferred pressure, excessive volatilization may occur. Above the upper preferred pressure, special high pressure equipment may be required and the process may be uneconomical.

The butadiene feedstream is contacted with the catalyst for a time sufficient to cyclodimerize the butadiene to vinylcyclohexene in high selectivity. Typically, the residence time is determined by the weight hourly space velocity, expressed in units of grams butadiene feed per gram catalyst per hour, or simply $hr^{-1}$. Typically, the weight hourly space velocity ranges from about 0.01 $hr^{-1}$ to about 100 $hr^{-1}$, preferably from about 0.1 $hr^{-1}$ to about 10 $hr^{-1}$, more preferably, from about 0.5 $hr^{-1}$ to about 5.0 $hr^{-1}$.

When 1,3-butadiene or substituted butadiene is contacted with the catalyst of this invention in the manner described hereinbefore, the butadiene is cyclodimerized to 4-vinylcyclohexene or a substituted derivative thereof. Typically, this process occurs with high selectivity, therefore, few if any by-products are produced. Polymerization of butadiene, for example, is usually small. It is typical to find less than about 1 mole percent of the converted butadiene in the form of polymeric butadienes. The chief by-products are tetrahydroethylnaphthalenes, which are also usually found in less than about 1 mole percent concentration.

For the purposes of this invention, the term "conversion" refers to the mole percent of butadiene or substituted butadiene which reacts to form products. Generally, in a continuous flow reactor the one pass conversion is at least about 30 mole percent. Preferably, the one pass conversion is at least about 50 mole percent, more preferably at least about 60 mole percent. Unconverted butadiene can be separated from the product stream via distillation and recycled back to the dimerization reactor.

For the purposes of this invention, the term "selectivity" refers to the mole percent of converted butadiene or substituted butadiene which forms vinylcyclohexene or a substituted derivative thereof. As noted hereinbefore, by-products are few. Consequently, the selectivity for vinylcyclohexenes is high. Typically, the selectivity for vinylcyclohexenes is at least about 95 mole percent, preferably, at least about 97 mole percent, more preferably, at least about 99 mole percent, and most preferably at least about 99.5 mole percent.

A convenient measure of the activity of the catalyst of this invention is given by the rate constant for the formation of vinylcyclohexene or substituted vinylcyclohexene. Generally, the dimerization process of this invention follows second order kinetics, as illustrated by a linear plot of inverse moles of butadiene in the reactor (1/BD) versus time. The slope of the plot yields the bimolecular rate constant, k, given in units of $(mole-hr)^{-1}$ for a standard test composition. A discussion of second order rate phenomena can be found in Kinetics and Mechanism by A. A. Frost and R. G. Pearson. John Wiley and Sons, Inc., 1961, pp. 8–20. In special cases, such as at high initial butadiene concentrations of at least about 40 mole percent in the feedstream, deviation from second order kinetics is observed. In this case and for the purposes of this invention, the second order rate constant is referred to as the "apparent" bimolecular rate constant.

The rate constant for the formation of vinylcyclohexene in the processes of this invention varies widely depending upon the process conditions and the form of the catalyst, specifically, the type of carrier and the method of catalyst preparation. Illustrative Example E-1(a–b) hereinbelow provides a general procedure for evaluating catalyst activity via measurement of the rate constant for the formation of vinylcyclohexene. A typical bimolecular rate constant (k) for the liquid phase dimerization process of this invention is at least about 0.1 $(moles-hr)^{-1}$ at 100° C. for a feed composition comprising 25 weight percent butadiene and 75 weight percent ethylbenzene. Preferably, the rate constant is at least about 0.2 $(moles-hr)^{-1}$, and for ion-exchanged catalysts may be as high as about 2.5 $(moles-hr)^{-1}$. Preferred rate constants will depend on economic considerations, and even rate constants as low as 0.1 $(moles-hr)^{-1}$ are commercially feasible provided that the lifetime of the catalyst is long, as is the case in the impregnated catalyst of this invention. Preferably, catalysts prepared by impregnation and by liquid-solid or vapor-solid reaction achieve a rate constant of at least about 0.5 $(moles-hr)^{-1}$ for the aforementioned process conditions and feed composition.

In accordance with the second process of this invention, a promoting amount of hydroxylic solvent causes the rate constant for the formation of vinylcyclohexene to increase, as compared with the rate constant of a control process. The control process is identical to the process of this invention with one exception. Rather than employing a promoting amount of hydroxylic solvent, the control process operates at a minimum of hydroxylic solvent. By "minimum of hydroxylic solvent" is meant that the concentration of hydroxylating solvent in the catalyst of the control is no greater than about 2 weight percent. In all other aspects the control process is identical to the process of this invention. For example, the control catalyst is prepared with the same components and same procedures as the catalyst of the invention with the exception that the catalyst is not treated with hydroxylic solvent. Moreover, the process conditions of the control reaction, including the butadiene feedstock, temperature, pressure, flow rate, reactor design, and the like, are identical to the conditions of the process invention.

When the rate constant for the formation of vinylcyclohexene of the second process of this invention is compared with the rate constant of the above-described control process, it is seen that the rate constant of the process of this invention is higher. The increase depends upon the specific process conditions and the specific catalyst employed and therefore varies widely. Increases in the rate constant as low as about 25 percent are possible, as are increases as high as about 500 percent. Preferably, the increase in rate constant is at least about 50 percent, more preferably at least about 100 percent, and most preferably, at least about 250 percent.

The following illustrative embodiments are representative of the process and catalyst of this invention, but are not intended to be limiting thereof. Unless otherwise noted, all percentages are given as weight percent.

EXAMPLE E-1

Preparation of Cu(I) Ion-exchanged Zeolite Catalysts

A copper(I) ion-exchanged zeolite catalyst is prepared according to the following general procedure: A developmental crystalline aluminosilicate zeolite Y with 15 percent silicate binder (UOP LZY-54, 140 g) is dried at 350° C. for 60 hr in a muffle furnace. (Bulk and framework $SiO_2Al_2O_3$ molar ratios of the zeolite are both 5/1.) The heated zeolite is loaded into a three-neck, one-liter glass reactor equipped with a dry ice condenser and solids addition funnel. The reactor system is flushed with pre-purified nitrogen and evacuated three times. Liquid ammonia is condensed into the reactor until the catalyst pellets are just covered; thereafter copper(I) iodide (37 g; 0.29 moles) is added to the reactor. Nitrogen is sparged into the reactor to effect agitation, and the ammonia is allowed to reflux for three hours. Afterwards, the liquid ammonia is removed from the bottom of the reactor and the pellets are washed once with ammonia. A second charge of copper iodide (37 g, 0.29 moles) and liquid ammonia is added and reflux is continued for another three hours. The reactor is drained and the pellets are washed twice with about 60 ml of liquid ammonia. The pellets are loaded into a tubular reactor and the residual ammonia is removed at 350° C. with flowing nitrogen yielding a dried copper(+1) ion-exchanged zeolite catalyst with a copper loading of 6.6 percent. The water content of the dried catalyst is 2.13 percent, as determined by thermogravimetric analysis (TGA). The dried catalyst is control sample C-1. Two samples of the dried catalyst (4.75 g) are allowed to adsorb water vapor from a wet nitrogen atmosphere for a time sufficient to obtain hydrated catalysts E-1-a and E-1-b having the water concentrations shown in Table I.

TABLE I

| Example | Wt. % $H_2O$ | k (mole-hr)$^{-1}$ |
| --- | --- | --- |
| C-1 | 2.130 | 0.420 |
| E-1-a | 10.900 | 1.930 |
| E-1-b | 14.000 | 0.531 |

Dimerization of Butadiene to Vinylcyclohexene E-1-a-b—Measurement of Rate Constant The control and hydrated catalysts (C-1, E-1-a and E-1-b) prepared hereinabove are tested in the dimerization of butadiene (BD) according to the following general procedure: The catalyst (4.75 g) is placed in an annular basket in a 300 cc Parr reactor equipped with overhead stirring, a sampling dip tube, and a thermocouple for measuring temperature. The reactor is further loaded with 100 cc of ethylbenzene. The reactor is sealed, and thereafter purged three times with 400 psig of nitrogen, and then vented to atmospheric pressure. Butadiene (28.9 g, 0.535 moles) is added as a liquid. The reactor is pressurized to 440 psig with nitrogen and the temperature is raised to 100° C. The contents are sampled at various times by emptying a sample loop into a pre-weighed, septum-sealed sample vial containing hexane, as a diluent, and an internal standard, and then analyzed on an FID capillary gas chromatograph. Vinylcyclohexene is formed in a selectivity of about 99 mole percent. The second order rate constant for the formation of vinylcyclohexene is determined by a least squares fit to data plotting inverse moles butadiene in the reactor (1/BD) versus time. The rate constants are set forth in Table I and plotted versus water concentration in FIG. 1.

It is observed that a copper(I) ion-exchanged faujasite zeolite catalyzes the cyclodimerization of butadiene to vinylcyclohexene in high selectivity. Furthers the rate constant of the control experiment C-1 is seen in FIG. 1 to be significantly less than the rate constant of the hydrated catalyst E-1-a and slightly less than the rate constant of the hydrated catalyst E-1-b. The rate constant is observed to peak at a water concentration of about 8 percent. FIG. 1 also shows that it is impractical to operate the cyclodimerization process with the catalyst of E-1-a-b at water concentrations less than about 2 percent or greater than about 15 percent.

EXAMPLE E-2

Preparation of Calcium(II) and Copper(II) Ion-exchanged Zeolite, Pre-reduced with Ammonia A pelletized zeolite Y (100 g; UOP LZY-54) bound with 15 percent silicate is ion-exchanged with 1.5 L of a 0.1M calcium acetate solution for 4 hr at 25° C. Thereafter, the ion-exchanged zeolite is washed with 3 L of deionized water, dried at 110° C. overnight and calcined at 500° C. for 18 hr. The pellets are ion-exchanged a second time with 2 L of the 0.1M cupric acetate solution for 18 hr. The ion exchange procedure is repeated twice for 2 hr each to give a concentration of 3.61 percent copper(II). The ion-exchanged zeolite is washed with 4 L of deionized water and dried a second time at 100° C. overnight. The dried zeolite is reduced with gaseous ammonia (5 vol. percent in nitrogen) for 1 hr at 250° C., and then stripped at that temperature for 30 min under a nitrogen flow. Samples of the reduced and dried pellets are hydrated to a predetermined concentration of water in a moist nitrogen atmosphere as set forth in Table II.

TABLE II

| Example E-2 | Wt. % $H_2O$ | k (mole-hr)$^{-1}$ |
| --- | --- | --- |
| a | 2.570 | 0.990 |
| b | 6.000 | 1.051 |
| c | 8.690 | 1.310 |
| d | 19.400 | 0.927 |

Cyclodimerization of Butadiene to Vinylcyclohexene Measurement of Rate Constant

The ion-exchanged, hydrated pellets E-2-a-d (4.0 g), prepared hereinabove, are employed as catalysts in the cyclodimerization of butadiene according to the procedure of E-1-a-b with the results shown in Table II and FIG. 1. Vinylcyclohexene is produced in a selectivity of at least 99 mole percent.

It is observed that a calcium and copper(II) ion-exchanged faujasite zeolite pre-reduced with ammonia catalyzes the cyclodimerization of butadiene to vinylcyclohexene in high selectivity. It is seen in FIG. 1 that the plot for Example E-2 is broad and flat, whereas the plot for Example E-1 is narrow and sharp. This comparison suggests that water affects the rate constant of catalyst E-1, which contains no calcium, more significantly than the rate constants of catalysts E-2, which contain calcium. However, the increase in rate constant for catalysts E-2 is observed over a wider range of water concentration than the increase observed for E-1. The plot also shows that it is impractical to practice the cyclodimerization process with catalysts E-2 at water concentrations greater than about 25 percent.

EXAMPLE E-3

Preparation of Copper(II)-Exchanged Zeolite, Pre-reduced with Hydrazine

Sodium zeolite Y-52 (77 g, Union Carbide), undried, is slurried in 250 cc of a 0.5M solution of cupric nitrate for 1 hour at room temperature. The mixture is filtered and washed once with 20 cc of deionized water. This procedure is repeated five times with the last set of washings being repeated until the filtrate is colorless. The resulting solid is dried for 2 hours in a nitrogen bled vacuum oven (20 mm Hg) at 110° C. The dried, ion-exchanged zeolite containing 8.78 percent copper (5 g, 6.9 mmoles $Cu^{+2}$) is added to 22 cc of a 0.35M solution of sodium hydroxide and the slurry is degassed with nitrogen for 30 minutes. An 85 percent solution of hydrazine hydrate (11.5 µl) is added to the slurry at 25° C, and an immediate color change to green is observed. After 30 minutes another 11.5 µl of the same hydrazine solution is added, and after another 30 minutes a third addition of hydrazine solution (11.5 µl) is added bringing the color to a yellow gold. The slurry is stirred for 2 hours and filtered, and the resulting solid is washed with water and dried in the nitrogen-purged vacuum oven for 2 hours at 110° C. to yield a copper(II) ion-exchanged zeolite pre-reduced with hydrazine. Samples of the above-identified zeolite are exposed to a moist atmosphere to obtain a predetermined moisture content as shown in Table III.

TABLE III

| Example | Wt. % $H_2O$ | k (mole-hr)$^{-1}$ |
|---------|--------------|---------------------|
| E-3-a   | 9.400        | 0.170               |
| E-3-b   | 12.500       | 1.590               |
| E-3-c   | 12.500       | 1.618               |
| E-3-d   | 12.500       | 1.613               |
| E-3-e   | 13.900       | 1.935               |
| E-3-f   | 22.04        | 0.810               |

Cyclodimerization of Butadiene to Vinylcyclohexene

The reduced compositions E-3-a–f (4.0 g each) are employed as catalysts in the cyclodimerization of butadiene according to the procedure of Example E-1-a–b, with the exception that the process temperature is 115° C. Results are set forth in Table III and are plotted in FIG. 1. It is observed that the copper ion-exchanged faujasite zeolite pre-reduced with hydrazine catalyzes the dimerization of butadiene to vinylcyclohexene in high selectivity. When Example E-3-a–f is compared with Example E-1-a–b, it is seen that the plots for each are both intense and sharp, but shifted along the x-axis (Wt. % $H_2O$) from each other. This result illustrates how the optimum water concentration varies with the method of preparing the catalyst. In addition, the plot shows that catalysts E-3-a–f, which do not contain calcium, are significantly more dependent on water concentration than catalysts E-2-a–d, which contain calcium. The plot also shows that it is impractical to run the dimerization process with catalyst E-3 at water concentrations less than about 9 percent and greater than about 24 percent.

EXAMPLE E-4

Preparation of Cu(II)-Impregnated Zeolite

Pellets (⅛" dia.) of a crystalline alumino-silicate zeolite (Union Carbide LZY-52) are made in ⅛" rubber tubing by isostatic compression at 30,000 psig of the as received solids without addition of a binder. This zeolite is in the sodium form and has bulk and framework $SiO_2/Al_2O_3$ ratios of 5/1. The pellets (5 g) are impregnated with 4.2 cc of a 1M aqueous copper(II) nitrate solution. The impregnation is carried out on a watch glass where liquid and pellets are quickly mixed, and the moist pellets are placed in a drying oven at 110° C. The pellets are gently stirred at the start of the drying period until visibly dry, and then they are dried further in the oven for several hours. The dried, impregnated zeolite contain., 5.5 percent copper. Thereafter, the zeolite is calcined under air at a temperature of 275° C. overnight to remove or destroy the nitrate anion and to dry the zeolite further. The dried zeolite contains less than 2.0 percent water and is employed as a control (C-4) in the dimerization of butadiene, as noted hereinafter. Samples of the dried catalyst are hydrated by exposure to ambient air, as noted hereinafter, until a predetermined water concentration is obtained, as determined by TGA and as set forth in Table IV.

TABLE IV

| Example | Wt. % $H_2O$ | k (mole-hr)$^{-1}$ |
|---------|--------------|---------------------|
| C-4     | 2.000        | 0.070               |
| E-4-a   | 3.400        | 0.110               |
| E-4-b   | 4.000        | 0.114               |
| E-4-c   | 4.800        | 0.170               |
| E-4-d   | 5.100        | 0.136               |
| E-4-e   | 5.300        | 0.170               |
| E-4-f   | 6.900        | 0.162               |
| E-4-g   | 8.900        | 0.186               |
| E-4-h   | 12.100       | 0.127               |
| E-4-i   | 9.800        | 0.169               |

Cyclodimerization of Butadiene to Vinylcyclohexene

The control C-4 and hydrated zeolites E-4-a–i, prepared hereinabove, are employed in the cyclodimerization of butadiene, as described in Example E-1-a–b. The zeolite is reduced to the active catalytic form in situ in the cyclodimerization process. After 4 hr into the cyclodimerization run and although the catalyst has not lost significant activity, the run is stopped and the catalyst is calcined at 275° C. under flowing air (22 cc/min) overnight. Thereafter the catalyst is exposed to ambient air until a predetermined water concentration is obtained. The hydrated catalyst is employed in the same dimerization reaction for another 4 hr, after which the run is stopped and the catalyst is recalcined and re-hydrated to a new water concentration. Selection of the water concentration is random, and not in in the order shown in Table IV. In such a manner a single batch of catalyst is run in the cyclodimerization, recovered, re-hydrated, and rerun in the dimerization to generate the data of Table IV, which data are plotted in FIG. 2. Vinylcyclohexene is produced in a selectivity of at least 99 mole percent.

Figure 2:
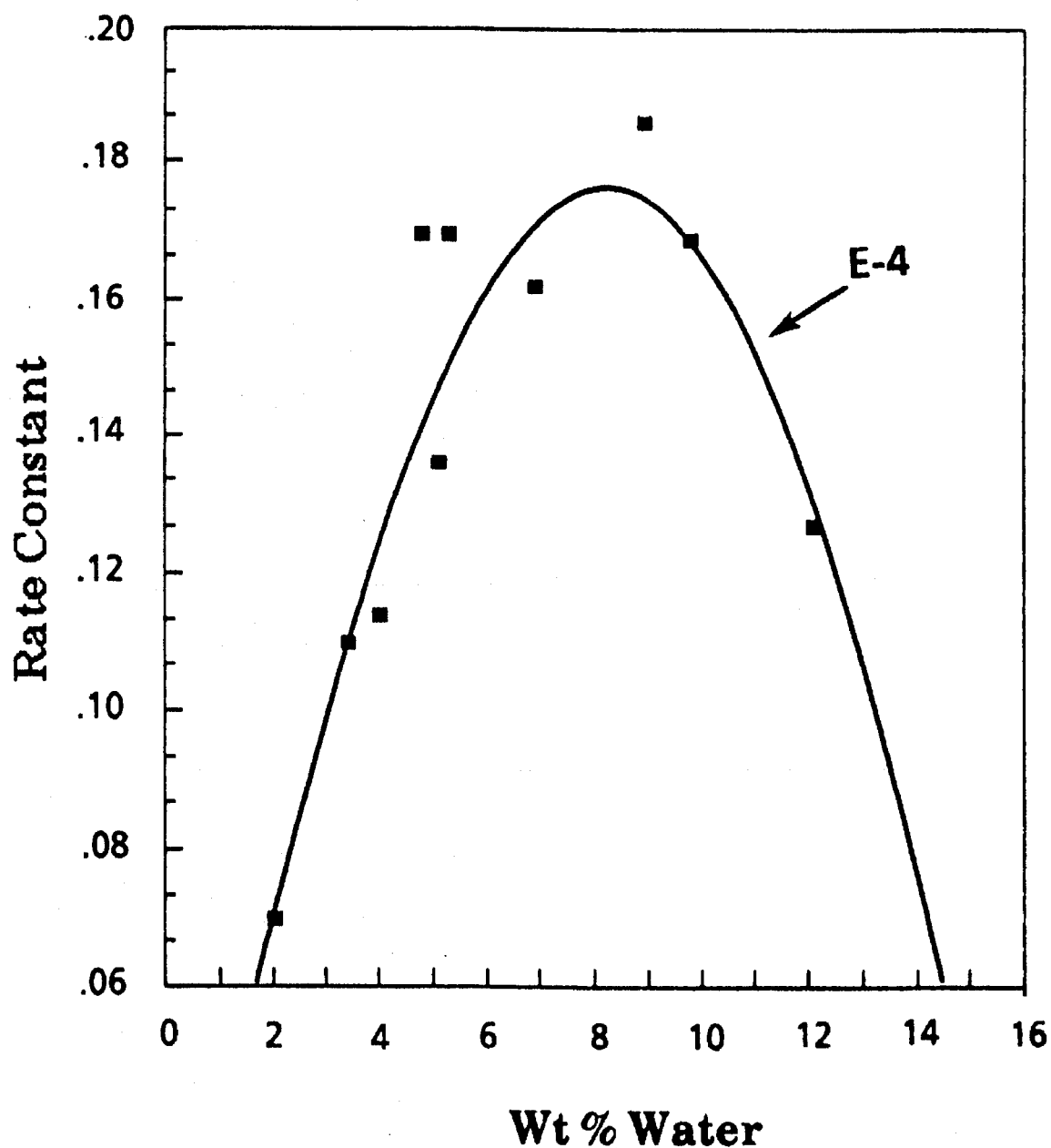

It is observed that the hydrated catalysts E-4-a–i achieve a significantly higher rate constant for the formation of vinylcyclohexene than the dried control catalyst C-4. Moreover, the rate constant is seen to peak at a water concentration of about 8 percent. FIG. 2 also shows that it is impractical to run the dimerization process with catalyst E-4 at a water concentration less than about 2 percent and greater than about 14 percent.

EXAMPLE E-5

Preparation of Impregnated, Butadiene Reduced Catalyst and Use Thereof in Cyclodimerization A catalyst is prepared with a dealuminated zeolite Y faujasite molecular sieve (UOP, LZY-20M) having a bulk $SiO_2/Al_2O_3$ molar ratio of 11.4 (22.1 for tetrahedral framework alumina), which is bound and pelletized with 20 percent inert silica binder. The pellets are dried for 2 hr at 110° C. A 1M aqueous solution of copper nitrate (5.0 g) is added to the dried pellets (5.0 g) to impregnate the pellets with Cu(II) salt to incipient wetness. The impregnated pellets are thereafter dried in an oven under air at 110° C. for about 4 hr, and then calcined in air at 275° C. for several hr. The calcined pellets are hydrated in humid air to a water content of 8 percent, as determined by TGA. The hydrated composition (4.2 g) is loaded into a stainless steel tubular reactor (½ inch i.d.) with a concentric thermocouple well, and thereafter the ends of the reactor are packed with glass beads. A liquid feed comprising 40 mole percent butadiene in ethylbenzene is pumped into the reactor at a rate of 7 g/hr. The pressure of the reactor is maintained at 200 psig. A recycle pump is placed between the entrance and exit of the reactor to provide a recycle of 10/1. It is noted that the butadiene feed reduces the Cu(II)-zeolite in situ to a Cu(I)-zeolite.

Deactivation of the catalyst is monitored. At 100° C. the butadiene conversion is 50 mole percent, as measured by an on-line gas chromatograph. The conversion remains constant within 3 percent over a 200 hr test period. A 3 mole percent loss in conversion corresponds to a catalyst half-life ($\tau\frac{1}{2}$) of 1000 hr, assuming pseudo-first order deactivation kinetics. The calculated rate constant at 100° C. is 0.2 (mole-hr)$^{-1}$. The temperature of the reactor is raised to 115° C. The conversion increases to 60 mole percent and remains constant within 3 percent over a 180 hr test period, thereby corresponding to a $\tau\frac{1}{2}$ of nearly 1000 hr. The results show that the Cu-impregnated faujasite catalyst reduced in situ in the dimerization reaction achieves a half-life greater than 500 hr and a rate constant greater than 0.1 (mole-hr)$^{-1}$.

EXAMPLE E-6

Preparation of Impregnated, Butadiene Reduced Catalyst and Use Thereof in Cyclodimerization An impregnated catalyst is prepared as in Example E-5, with the exception that the copper content is 7.5 percent (dry basis). The catalyst is hydrated to 8.5 percent water concentration. The catalyst (75 g) is placed in a stainless steel basket in a 1 l continuously stirred tank reactor. The reactor is heated to 100° C., and a feedstream comprising butadiene, n-butane, and ethylbenzene in a molar ratio of 1:1:0.5 is passed into the reactor at a feed rate of 160 g/hr and a pressure of 500 psig. The butadiene conversion, which remains essentially constant for the test time of 100 hr, is 43 mole percent, corresponding to a $\tau\frac{1}{2}$ greater than 500 hr. The calculated rate constant is 0.3 (mole-hr)$^{-1}$. On conversion to a feedstream comprising butadiene and n-butane in a molar ratio of 1:1 for a test time of 150 hr, comparable results are obtained with a calculated $\tau\frac{1}{2}$ of greater than 1000 hr. The half-life $\tau\frac{1}{2}$ remains greater than 1000 hr on increasing the reaction temperature to 115° C. The results show that a copper impregnated faujasite catalyst reduced in situ in the dimerization reaction achieves a rate constant greater than 0.1 (mole-hr)$^{-1}$ and maintains excellent lifetime under different feedstreams and at different reaction temperatures.

EXAMPLE E-7

Preparation of Impregnated, Butadiene Reduced Catalyst and Use Thereof in Cyclodimerization An impregnated catalyst is prepared as in Example E-5, with the exception that the inert silica binder content is 15 percent. The catalyst is employed in the dimerization of butadiene in the reactor and under the process conditions described in Example E-5. The butadiene conversion is 48 mole percent, and there is no detected deactivation of the catalyst within the 100 hr test period. The catalyst is subjected to regeneration conditions comprising burning in air at 275° C. for several hours, followed by rehydration to 8 percent water concentration. The regenerated catalyst is re-run in the dimerization reaction for 100 hr. The used catalyst is regenerated and re-run in the dimerization reaction a second time. After a third regeneration the catalyst is re-run again in the dimerization reaction under the conditions of Example 5. The butadiene conversion is 49 mole percent with no deactivation during the test time of 240 hr. The calculated $\tau\frac{1}{2}$ is greater than 1000 hr and the calculated rate constant is 0.2 (mole-hr)$^{-1}$. The experiment shows that the Cu-impregnated faujasite catalyst achieves a rate constant greater than 0.1 (mole-hr)$^{-1}$ and a half-life greater than 500 hr. Moreover, the data show that the catalyst is easily regenerated and that oxidation and burn-off do not adversely affect the catalyst's performance.

EXAMPLE E-8

Preparation of Impregnated, Butadiene Reduced Catalyst and Use Thereof in Cyclodimerization An impregnated catalyst is prepared as in Example E-5, with the exception that the binder is alumina (UOP) in a concentration of 20 percent. The catalyst is evaluated in the dimerization of butadiene as in Example E-5. A conversion of 50 mole percent is obtained with essentially no deactivation over a 200 hr test period. The calculated $\tau\frac{1}{2}$ is greater than 1000 hr and the rate constant is 0.2 (mole-hr)$^{-1}$. This experiment, taken with Examples E-5, E-6, and E-7, shows that different inert binders do not materially affect the catalyst's performance.

Comparative Experiment CE-1

An impregnated catalyst is prepared as in Example E-5, with the exception that the LZ-20M sieve is replaced by a zeolite Y-54 sieve (UOP) having bulk and framework $SiO_2/Al_2O_3$ molar ratios of 5/1. The catalyst is evaluated in the dimerization of butadiene as in Example E-5 using a feed mixture of butadiene (BD) and ethylbenzene (EB) in a BD:EB molar ratio of 1:1.5. The catalyst deactivates with a measured $\tau\frac{1}{2}$ of 25 hr. The calculated rate constant is 0.4 (mole-hr)$^{-1}$. When Comparative Example E-1 is compared with Example E-5, it is seen that the combination of low bulk and low framework $SiO_2/Al_2O_3$ molar ratios of the comparative catalyst does not lessen activity, but is detrimental to the lifetime and stability of the catalyst.

EXAMPLE E-9

Preparation of Impregnated, Butadiene Reduced Catalyst and Use Thereof in Cyclodimerization A catalyst is prepared as in Example E-5, with the exception that samples of the catalyst are hydrated as in Table V.

TABLE V

| Example | Wt. % H$_2$O | k (mole-hr)$^{-1}$ |
| --- | --- | --- |
| E-9-a | 2.0 | 0.21 |
| E-9-b | 3.6 | 0.21 |
| E-9-c | 6.5 | 0.31 |
| E-9-d | 10.5 | 0.25 |
| E-9-e | 14.2 | 0.23 |
| E-9-f | 3.4 | 0.27 |

Figure 3:
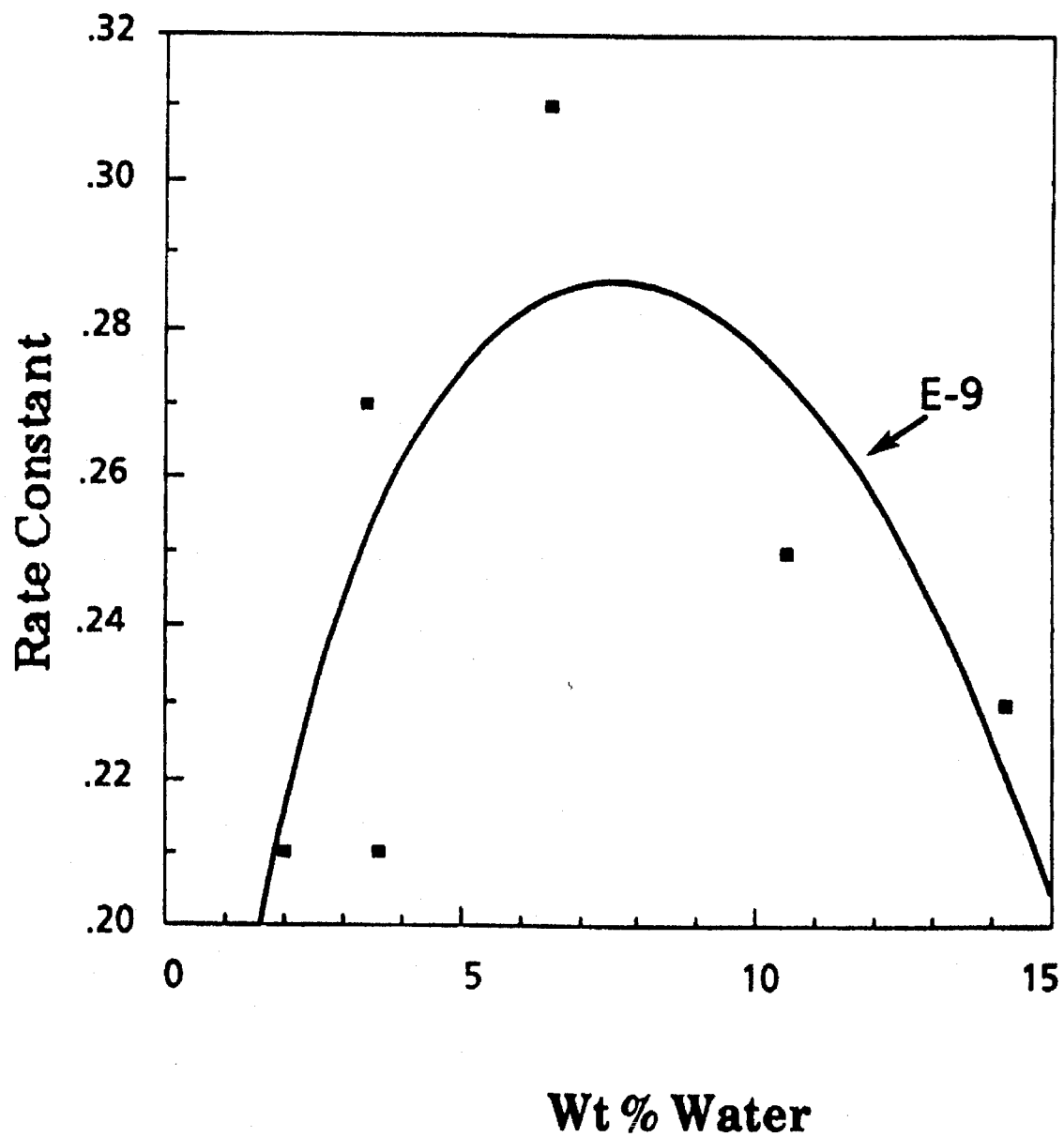

The catalysts are evaluated in the cyclodimerization of butadiene according to Example E-1-a–b with the results shown in Table V and FIG. 3. It is seen that maximum catalyst activity is achieved at a water concentration of about 7 to 8 percent.

EXAMPLE E-10

Preparation of Impregnated, Butadiene Reduced Catalyst and Use Thereof in Cyclodimerization Three impregnated catalysts E-10-a–c are prepared as in Example E-5, with the exception that the LZY-20M sieve is replaced by a SA-15AE sieve (UOP) having a bulk $SiO_2/Al_2O_3$ molar ratio of 37 and a framework $SiO_2/Al_2O_3$ molar ratio of 40, and with the further exception that the water concentration is adjusted as in Table VI. The catalysts are tested in the dimerization of butadiene as in Example E-1-a–b with the exception that the temperature is 115° C. Results are set forth in Table VI.

TABLE VI

| Example | Wt. % H$_2$O | k (mole-hr)$^{-1}$ |
|---|---|---|
| E-10-a | 1.7 | 0.053 |
| E-10-b | 5.6 | 0.068 |
| E-10-c | 8.0 | 0.069 |

The τ½ of catalyst E-10-c is evaluated using the procedure of Example E-5 and is found to be greater than 1000 hr. It is seen that the impregnated catalysts having both bulk and framework $SiO_2/Al_2O_3$ molar ratios of about 40 achieve long lifetime in the cyclodimerization process. Although the rate constants are observed to be somewhat low at 115° C. the process can be run at a slightly higher temperature to achieve a rate constant of 0.1 (mole-hr)$^{-1}$ and a τ½ of at least 200 hr.

EXAMPLE E-11

Preparation of Impregnated, 1-Butene Reduced Catalyst and Use Thereof in Cyclodimerization A catalyst is prepared from a dried zeolite Y molecular sieve (UOP, LZY-20M) having a bulk $SiO_2/Al_2O_3$ molar ratio of 11.4 (22.1 for tetrahedral framework alumina), which is bound and pelletized with 20 percent alumina binder. The pellets are impregnated with an aqueous solution of copper nitrate such that the copper concentration on the pellets is 5.6 percent. The impregnated pellets are dried in an oven under air and then calcined in air at 275° C. The calcined pellets are reduced at 120° C. under a stream of nitrogen containing 20 volume percent 1-butene until the observed exotherm is passed. After reduction the pellets are stripped under a flow of nitrogen at 250° C. for 1.5 hr to remove excess butene yielding a catalyst comprising a copper(I)-impregnated zeolite Y. The concentration of water on the catalyst is 3.5 percent.

The catalyst prepared hereinabove is employed in the liquid phase cyclodimerization of butadiene according to the procedure of Example E-1-a–b yielding at 100° C a rate constant of 0.65 (mole-hr)$^{-1}$. The catalyst is also employed in the process of Example E-5, yielding τ½ greater than 500 hr. It is seen that the impregnated catalyst, reduced with 1-butene, has both good activity and long lifetime.

EXAMPLE E-12

Preparation of Impregnated, Propylene Reduced Catalyst and Use Thereof in Cyclodimerization A copper(I)-impregnated zeolite Y is prepared according to the procedure of Example E-11, with the exception that the copper(II)-impregnated precursor is reduced with propylene. The concentration of water on the catalyst is 2.2 percent. The catalyst is employed in the cyclodimerization of butadiene according to the procedure of Example E-1-a–b yielding at 100° C. a rate constant of 0.65 (mole-hr)$^{-1}$. It is seen that a catalyst active in the dimerization of butadiene can be prepared by reduction with 1-propylene.

EXAMPLE E-13

Preparation of Catalyst by Impregnation and Solid Reaction; Use in Cyclodimerization A sample of faujasite Y zeolite (UOP LZY-20M) is impregnated with Cu(II) ions and calcined as in Example E-5 hereinabove. A solid mixture is prepared comprising 76 percent impregnated zeolite and 24 percent cuprous chloride. The solid mixture is heated at 650° C. for 1 hr under nitrogen flowing at a rate of 150 cc/min. The resulting Cu(I)-zeolite catalyst (93.4 g), prepared by both impregnation and solid reaction, is placed in a stainless steel basket in a 1 l continuously stirred tank reactor. The cyclodimerization is run at the following process conditions: 100° C., 500 psig, feedstream flow rate 176 g/hr. The feedstream comprises butane and butadiene in a molar ratio of 1:1. Butadiene conversion remained constant at 46 mole percent during the 100 hr test run corresponding to a τ½ greater than 1000 hr. The rate constant is calculated to be 0.38 (mole-hr)$^{-1}$. It is seen that a catalyst prepared by impregnation and solid reaction exhibits both good activity and long lifetime.

EXAMPLE E-14

A solid mixture comprising 71 percent zeolite Y (UOP LZ-20M) and 29 percent cuprous chloride is heated at 650° C. under nitrogen for 1.5 hr. Thereafter, the catalyst is employed in the cyclodimerization of butadiene as in Example E-5. The catalyst achieves a τ½ of 250 hr and a calculated rate constant of 0.32 (mole-hr)$^{-1}$. The catalyst is regenerated by heating in oxygen at 325° C., thereafter reducing under ammonia at 350° C., and finally stripping excess ammonia under a flow of nitrogen at 350° C. The regenerated catalyst is re-tested in the cyclodimerization of butadiene as in Example E-5. The catalyst achieves a τ½ greater than 500 hr and a calculated rate constant of 0.34 (mole-hr)$^{-1}$. It is seen that a catalyst prepared by solid reaction exhibits both good activity and long lifetime, and the catalyst is also regenerable.

What is claimed is:

1. A catalyst composition comprising a copper(I)-impregnated aluminosilicate zeolite wherein the zeolite is selected from the group consisting of faujasites, zeolite L, and zeolite Ω, and wherein the zeolite is characterized by a silica to bulk alumina molar ratio in the range from about 12 to about 50 and a silica to framework alumina molar ratio of at least about 15, and wherein optionally, the catalyst contains a binder, the composition being prepared by a process comprising (a) drying an aluminosilicate zeolite to remove water, the zeolite being selected form the group consisting faujasites, zeolite L, and zeolite Ω, and being characterized by a silica to bulk alumina molar ratio in the range from about 12 to about 50 and a silica to framework alumina molar ratio of at least about 15, (b) impregnating the dried zeolite with a solution containing a copper(II) salt, (c) calcining the copper(II)-impregnated zeolite under oxygen at a temperature between about 200° C. and about 325° C. under conditions such that the anion of the salt is removed, and (d) reducing the calcined copper(II)-impregnated zeolite with an olefinic hydrocarbon such that a portion of the copper(II) ions are converted to copper(I).

2. The catalyst of claim 1 wherein the bulk $SiO_2/Al_2O_3$ molar ratio ranges from 12 to 30 and wherein the framework $SiO_2/Al_2O_3$ molar ratio is at least 22.

3. The catalyst of claim 1 wherein the zeolite is a faujasite containing water in a concentration in the range from 3 to 14 weight percent.

4. The catalyst of claim 1 wherein a binder of alumina or silica is employed.

5. The composition of claim 1 wherein in the preparation of the composition the calcined copper(II)-impregnated zeolite is treated with a hydroxylating solvent prior to reduction.

6. The catalyst composition of claim 1 wherein the zeolite is zeolite Y.

7. The catalyst composition of claim 1 wherein the concentration of copper ions ranges from about 0.1 to about 15 weight percent.

8. The catalyst composition of claim 1 wherein the catalyst is prepared by a method comprising (a) drying an aluminosilicate zeolite at a temperature between about 50° C. and about 450° C. to remove water, the zeolite being selected from the group consisting of faujasites, zeolite L and zeolite Ω, and being characterized by a silica to bulk alumina molar ratio in the range from about 12 to about 45 and a silica to framework alumina molar ratio of at least about 15, (b) impregnating the dried zeolite with a solution containing copper(II) nitrate, acetate, or sulfate, (c) calcining the copper(II)-impregnated zeolite under oxygen at a temperature between about 200° C. and about 325° C. such that the anion of the salt is removed, and (d) reducing the calcined copper(II)-impregnated zeolite in the presence of an olefinic hydrocarbon at a temperature from about 100° C. to about 140° C. such that a portion of the copper(II) ions are converted to copper(I).

9. The catalyst composition of claim 8 wherein the catalyst is prepared by (d) reducing the calcined copper(II)-impregnated zeolite in the presence of butadiene, propylene or 1-butene.

10. The catalyst composition of claim 8 wherein the zeolite is zeolite Y, and wherein prior to the reduction step (d), the calcined copper(II)-impregnated zeolite is hydroxylated so as to give a water concentration between 3 and about 14 weight percent, and wherein the reduction step (d) is carried out under butadiene.

11. The catalyst composition of claim 8 wherein the zeolite is zeolite Y, and wherein prior to the reduction step (d), the calcined copper(II)-impregnated zeolite is either not hydroxylated or is hydroxylated so as to give a water concentration no greater than about 6 weight percent, and wherein the reduction step (d) is carried out under 1-butene or propylene.

12. The catalyst composition of claim 1 wherein the concentration of copper ions ranges from about 3 to about 8 weight percent.

13. A process of preparing a catalyst composition comprising (a) drying an aluminosilicate zeolite to remove water, the zeolite being selected from the group consisting of faujasites, zeolite L and zeolite Ω, and being characterized by a silica to bulk alumina molar ratio in the range from about 12 to about 50 and a silica to framework alumina molar ratio of at least about 15, (b) impregnating the dried zeolite with a solution containing a copper(II) salt, (c) calcining the copper(II)-impregnated zeolite under oxygen at a temperature between about 200° C. and about 325° C. under conditions such that the anion of the salt is removed, and (d) reducing the calcined copper(II)-impregnated zeolite with an olefinic hydrocarbon such that a portion of the copper(II) ions are converted to copper(I).

14. The process of claim 13 wherein the zeolite is zeolite Y.

15. The process of claim 13 wherein the zeolite is impregnated with a solution of copper nitrate, sulfate or acetate.

16. The process of claim 13 wherein the zeolite is reduced in the presence of butadiene, propylene or 1-butene.

17. The process of claim 13 wherein the the calcined copper(II)-impregnated zeolite is hydroxylated prior to the reduction step (d).

* * * * *